(12) United States Patent
Wallman et al.

(10) Patent No.: US 6,192,768 B1
(45) Date of Patent: Feb. 27, 2001

(54) FLOW-THROUGH SAMPLING CELL AND USE THEREOF

(75) Inventors: Lars Wallman; Johan Drott; Johan Nilsson; Thomas Laurell; Staffan Nilsson, all of Lund (SE)

(73) Assignee: Pharmacia Biotech AB, Uppsala (SE)

( * ) Notice: Subject to any disclaimer, the term of this patent is extended or adjusted under 35 U.S.C. 154(b) by 0 days.

(21) Appl. No.: 08/981,236

(22) PCT Filed: Jun. 7, 1996

(86) PCT No.: PCT/SE96/00750

§ 371 Date: Feb. 25, 1998

§ 102(e) Date: Feb. 25, 1998

(87) PCT Pub. No.: WO97/01085

PCT Pub. Date: Jan. 9, 1997

(30) Foreign Application Priority Data

Jun. 21, 1995 (SE) .................................... 9502251

(51) Int. Cl.[7] ..................................................... G01N 1/20
(52) U.S. Cl. ................................... 73/864.83; 73/864.84; 73/864.33; 73/863; 73/863.31
(58) Field of Search ........................... 73/864.33, 864.34, 73/864.73, 864.83, 864.84, 863.73, 863.71, 863.72, 863, 864, 863.31, 863.32, 863.33

(56) References Cited

U.S. PATENT DOCUMENTS

| | | | |
|---|---|---|---|
| 3,775,058 | 11/1973 | Bush | 436/51 |
| 5,270,212 | * 12/1993 | Horiuchi et al. | 73/864.83 X |
| 5,338,688 | 8/1994 | Deeg et al. | 436/180 |
| 5,351,563 | * 10/1994 | Koppf et al. | 73/864.84 |
| 5,650,577 | * 7/1997 | Nagai et al. | 73/864.83 X |
| 5,738,133 | * 4/1998 | Seki et al. | 73/864.84 |

FOREIGN PATENT DOCUMENTS

| | | |
|---|---|---|
| 0119573 | 9/1984 | (EP) . |
| 0268237 | 5/1988 | (EP) . |
| 0668500 | 8/1995 | (EP) . |
| WO9301485 | 1/1993 | (WO) . |

OTHER PUBLICATIONS

Nilsson et al., Journal of Biochemical and Biophysical Methods, 27 181–190, (1993 month not given) "A flow–through microsampling device applied to an ion–exchange chromatography system".

* cited by examiner

Primary Examiner—Thomas P. Noland
(74) Attorney, Agent, or Firm—Birch, Stewart, Kolasch & Birch, LLP

(57) ABSTRACT

A sampling cell of flow-through type and use of such a sampling cell. The sampling cell is preferably manufactured by etching of silicon wafers. It is especially useful for continuous picovolume sampling in an analytical flow. The pressure pulse generator (9) generates pulses directly into a flow channel (3). The flow channel (3) is preferably formed by a first basin (4) in a first structure (1) and a second basin (5) in a second structure (2). In a first embodiment the pressure pulse generator (9) comprises at least one piezo-ceramic disc and/or devices acting by way of magnetostrictive, electrostatical or electromechanical forces and/or devices acting by way of thermal expansion. Method of directing samples from a flow-through sampling cell by establishing a difference in electrical potential between the liquid in the flow-through sampling cell and the object to which the samples are to be directed. Use of a flow-through sampling cell for coating of surfaces, especially for achieving biospecific surfaces, for extracting samples from a continuous liquid flow, for extracting a precise sample amount by collecting a defined number of samples or for injecting samples for electrophoresis, especially capillary electrophoresis, and for electrochromatography.

35 Claims, 6 Drawing Sheets

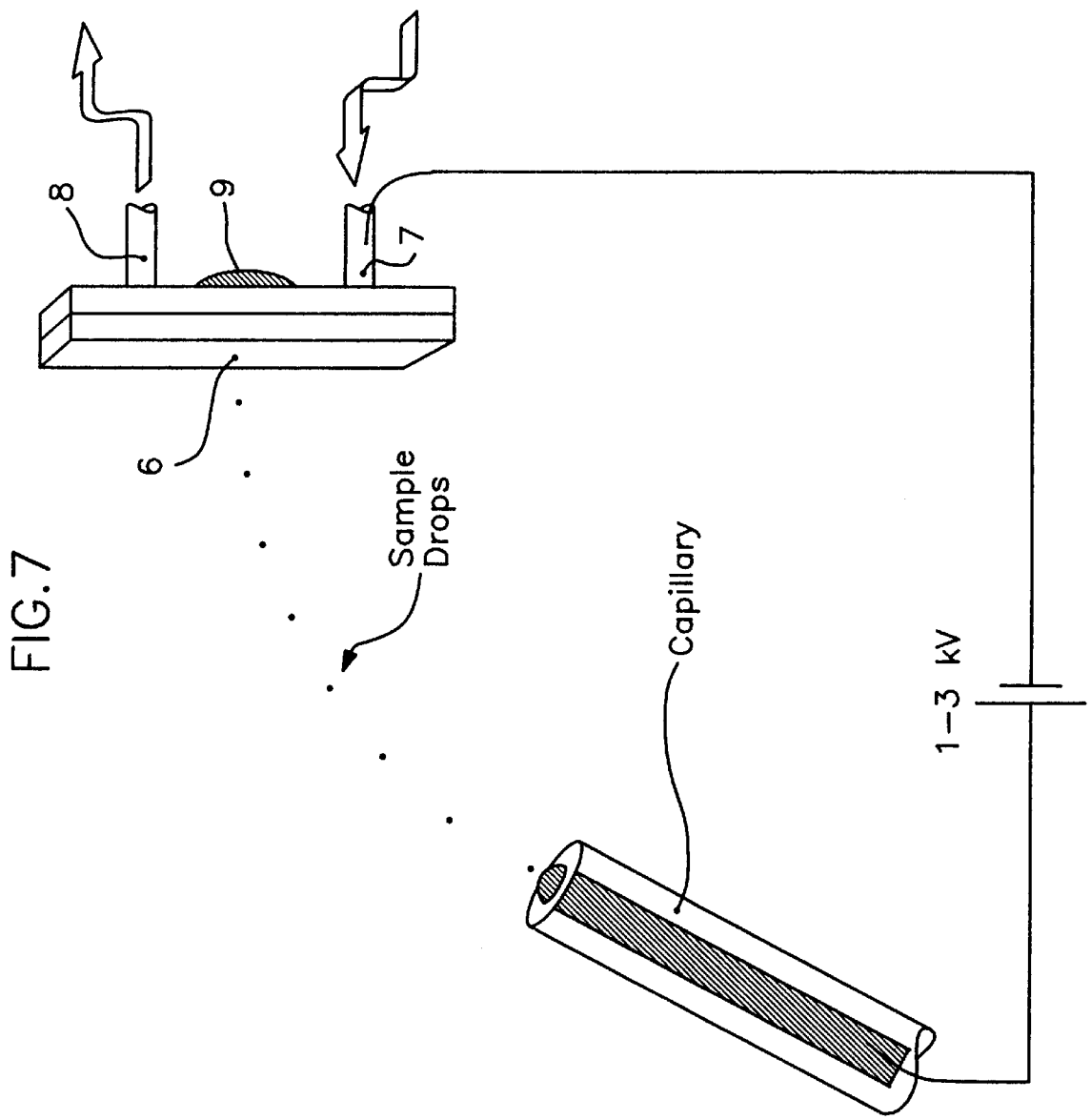

FLOW-THROUGH SAMPLING CELL AND USE THEREOF

This application is the national phase under 35 U.S.C. 371 of PCT Application No. PCT/SE96/00750 filed on Jun. 7, 1996, which designated the United States.

This invention relates to a sampling cell of flow-through type, a method for directing samples from such a sampling cell and use of such a sampling cell. The sampling cell is preferably manufactured by etching of silicon wafers. It is especially useful for continuous picovolume sampling in an analytical flow or for picovolume deposition of specific chemicals.

1. Background and Prior Art

Micro sample extraction is useful in e.g. fraction determination from protein separation systems. The sample extration and the fraction determination are tedious procedures, often including test tube matrix handling followed by analysis through e.g. gel electrophoresis before a final fraction identification is achieved.

Ref. 1 discloses a known sampling tool for fraction identification, being a flow-through cell comprising an orifice type nozzle and a piezo-ceramic disc glued onto a brass membrane. The brass membrane bends when a voltage is applied across the piezo-ceramic disc. The bending brass membrane creates a pressure pulse in a conical fluid-filled chamber which in turn transmits the pressure pulse onto a teflon membrane in the wall of the flow channel. Finally the pressure pulse, essentially unaffected, passes the teflon membrane and arrives in the fluid in the flow channel from which micro samples, i.e. small drops of the fluid, are ejected through the orifice type nozzle. This sampling tool is manufactured by conventional mechanical methods. This prior art sampling tool is schematically shown in the below FIG. 1 and 2.

Ref. 2 discloses an ink-drop generator comprising a piezo-ceramic layer generating a pressure pulse in a liquid-filled pressure channel. Anyhow this device is not of the flow-through type and can not be used for extracting samples from a continuous flow.

2. Advantages over Prior Art

The present invention relates to a sampling cell of flow-through type, i.e. a sampling cell with at least one flow inlet and at least one flow outlet from which samples are extracted from at least one sample emerging orifice, this orifice being separated from the flow inlet and the flow outlet. A sampling cell of flow-through type thus differs from other sampling cells, of non flow-through types, such as those wherein the flow outlet also serves as sample emerging orifice.

The above described tool for micro sampling according to Ref. 1 has some disadvantages, such as transmission of the pressure pulse through an intermediate chamber and through two separate membranes, rather large dead volumes, risk for sticking of pressure pulse absorbing bubbles within the tool due to the hollow part adjacent the orifice type nozzle, low resonance frequency due to the large overall dimensions of the tool, adherence of liquid to the area around the exit side of the orifice type nozzle, need for separate filling of the conical fluid-filled chamber, need for regular exchange of the teflon membrane, requirements for tightening around the teflon membrane, and comparably complicated and expensive manufacturing.

U.S. Pat. No. 5,338,688 (ROLF DEEG ET AL.) discloses a method for metered application of a biochemical analytical liquid to a target. Anyhow the device used is not of the flow-through type. Furthermore the method is limited to ejection of small liquid volumes through heating and subsequent evaporation of the liquid. Such heating may destroy the characteristics of the liquid.

U.S. Pat. No. 3,775,058 (BRIAN BUSH) discloses method and apparatus for mixing liquids. Anyhow the apparatus used is not of the flow-through type. Furthermore the apparatus requires means for electrostatically charging droplets to be formed by the apparatus.

EP 119 573 A1 (MILES LABORATORIES, INC.) discloses microdroplet dispensing apparatus and method. Also in this reference the apparatus used is not of the flow-through type.

The sampling cell according to the present invention has inter alia the following advantages over prior art devices:

- the sample emerging orifice (6) is placed directly in the wall of the flow channel, which provides for a very smooth channel, thus minimizing the risk for sticking of pressure pulse absorbing bubbles within the cell;
- small dead volumes which implies small losses when changing the liquid in the flow channel (3), in turn being beneficial when expensive liquids to be analyzed are handled;
- bandbroadening due to dead volume is reduced;
- in the present silicon micro-machined sampling cell the pressure pulse is generated directly on the walls of the flow channel while in prior art flow-through cells, such as the cell according to Ref. 1, the actuating means act on a fluid chamber which in turn transmits the pressure pulse to the flow cell via a membrane;
- small drops are often required. With the present silicon based sampling cell smaller drops can be generated than with prior art sampling cells. This is due to the fact that smaller and more precise holes can be made by etching in silicon than in cells being manufactured with conventional mechanical methods;
- the sampling cell is preferably made entirely of silicon, which is a uniform, inert and biocompatible material being hydrophilic when oxidized;
- the silicon parts may easily be chemically modified to adjust their surface properties.

OBJECTS OF THE INVENTION

A first object of the present invention is a sampling cell without the above disadvantages in accordance with claim 1.

Further objects of the invention are different embodiments of the sampling cell of claim 1.

Still further objects of the invention are different uses of the sampling cell and a method of directing samples emerging from the sampling cell.

SHORT DESCRIPTION OF THE FIGURES

The same figures, when denoted by reference signs, are in the description as well as in the drawings denoted by the same reference signs.

Figure 1:
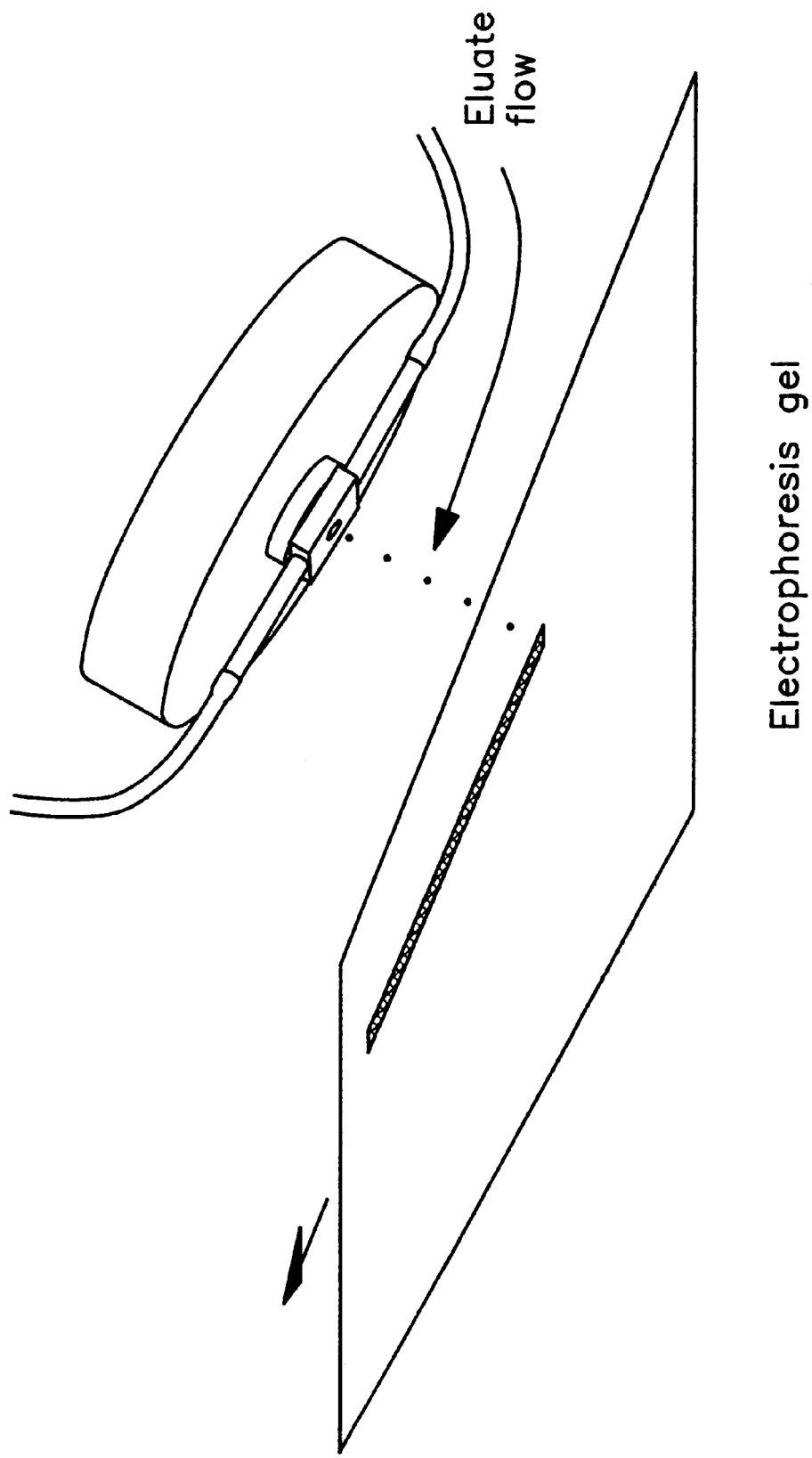
FIG. 1 shows in perspective a schematic view of a prior art micro sample tool in accordance with Ref. 1 in use for depositing microdrops of the eluate from an ion exchange column into an electrophoresis gel.
Figure 2:
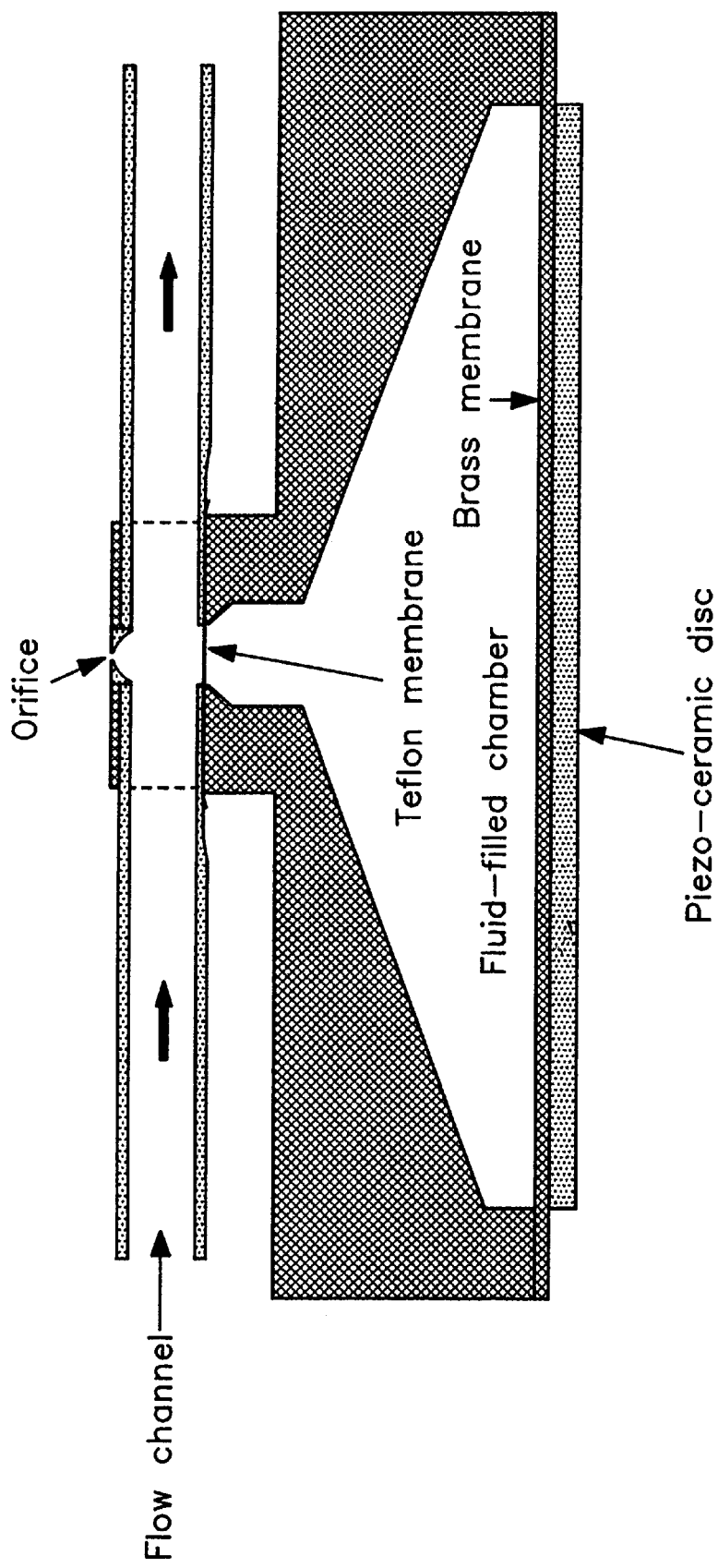
FIG. 2 shows in cross-section a schematic side view of the prior art micro sample tool in accordance with Ref. 1 and FIG. 1.
Figure 3:
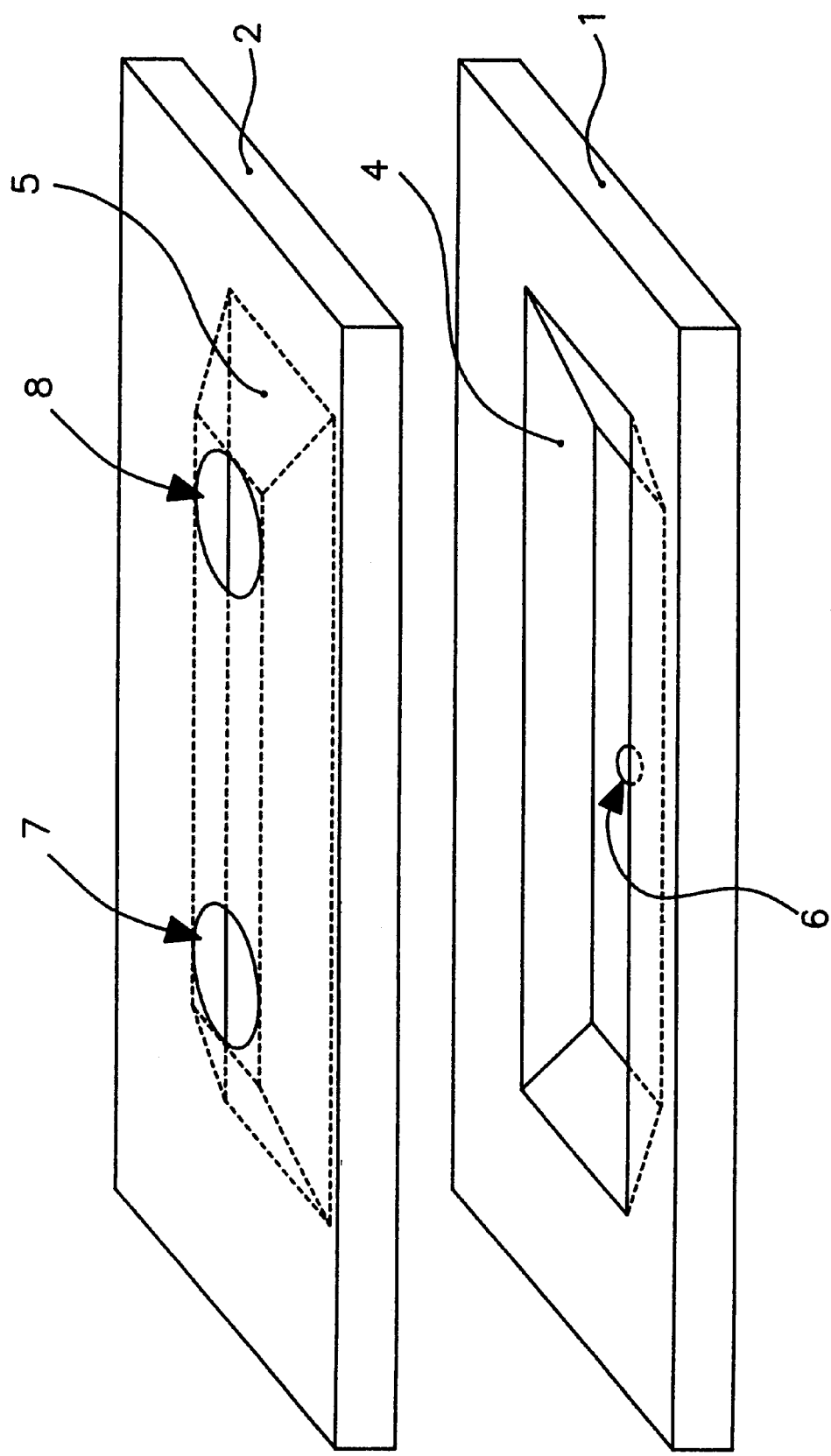

FIG. 3 shows in perspective and partly in cross-section a schematic view of a first embodiment of a sampling cell according to the present invention comprising a first structure (1) and a second structure (2), here seen somewhat separated from each other, while being attached to one another when in use. In the first structure (1) is formed a first basin (4) and in the second structure (2) is formed a second basin (5). The basins (4, 5) together form a flow channel (3). The first structure (1) has at least one sample emerging orifice (6). The second structure (2) has at least one flow inlet (7) and at least one flow outlet (8).

Figure 4:
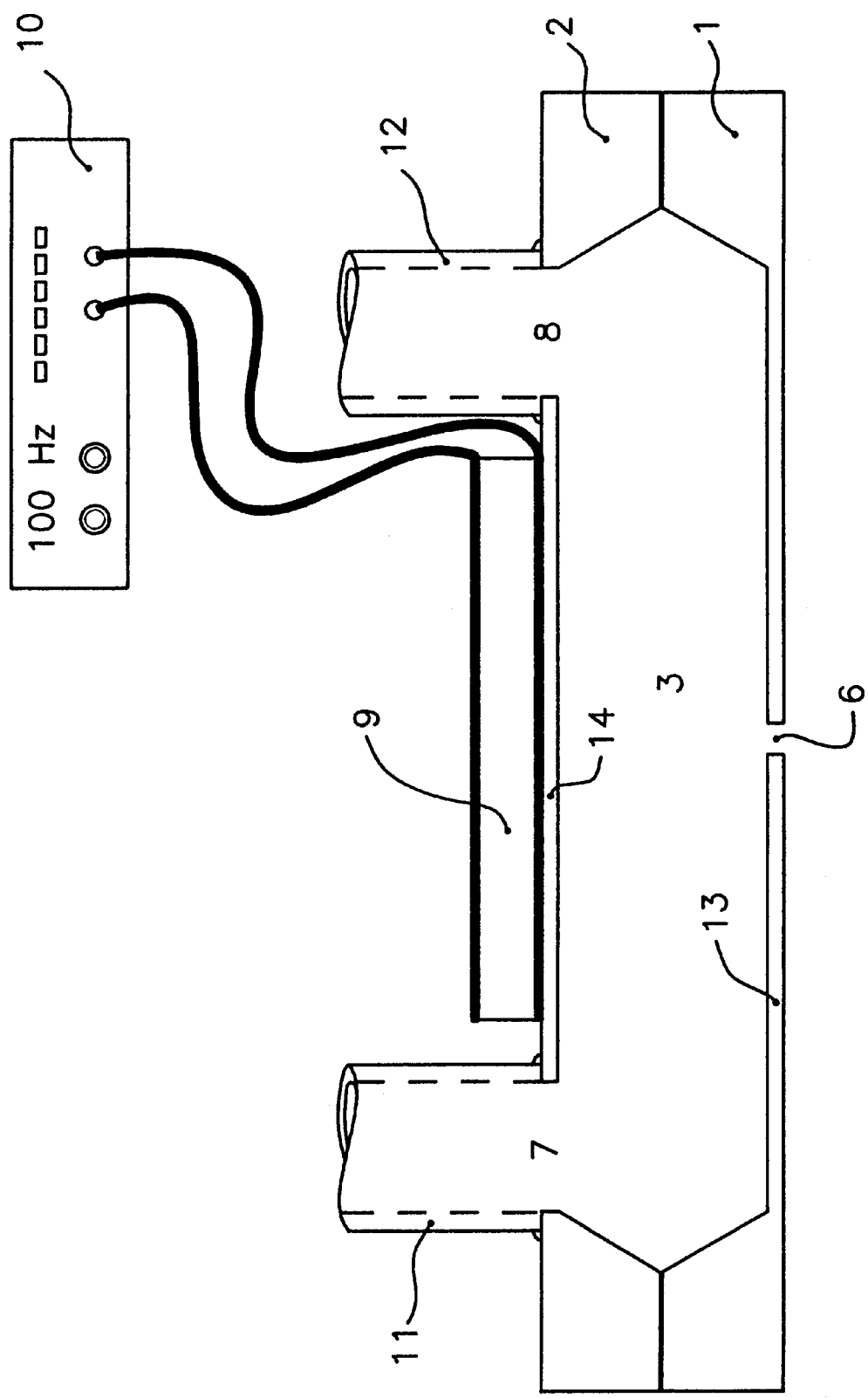

FIG. 4 shows in cross section a schematic side view of the first embodiment of FIG. 3 with a pressure pulse generating piezo-ceramic disc (9) attached to a pulse generator (10), a first silicone tube (11) attached to the flow inlet (7) and a second silicone tube (12) attached to the flow outlet (8). The first basin (4) defines a first silicon membrane (13) in the first structure (1) and the second basin (5) defines a second silicon membrane (14) in the second structure (2).

Figure 6:
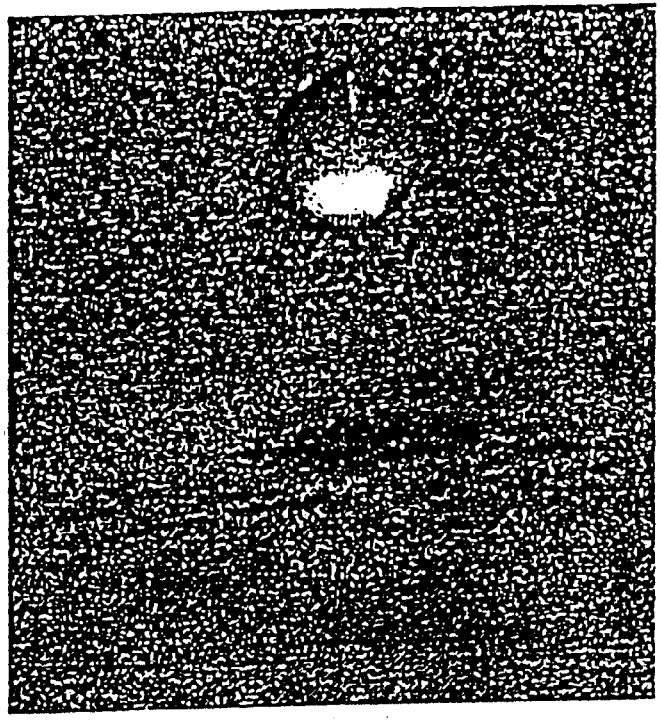
Figure 5:

FIGS. 5 and 6 are photograps showing ejection of drops, having a diameter of 40 µm, from the sample emerging orifice (6) of the first embodiment of the invention of the above FIG. 3 and 4.

FIG. 7 shows in perspective and partly in cross-section an embodiment of the present invention in which the direction of the emerging samples is controlled in accordance with the below Example 2.

DETAILED DESCRIPTION OF THE INVENTION

The following examples, with reference primarily to FIGS. 3–7, are intended to illustrate but not to limit the scope of the invention.

EXAMPLE 1

A sampling cell was manufactured from a first structure (1) and a second structure (2) which were fabricated on the same (100)-silicon wafer using anisotropic KOH etching. In the first structure (1) was formed a first basin (4), being 2 mm wide, 15 mm long and 350 µm deep. In the second structure was formed a second basin (5) having the same dimensions as the above first basin (4). In the first structure (1) was etched a sample emerging orifice (6) through the wafer approximately at the centre of the first basin (4). The sample emerging orifice (6) had a diameter of 60 µm and was in use serving as a sampling nozzle. In the second structure (2) was etched two holes, each having a diameter of 2 mm, through the silicon wafer at each end of the second basin (5), these holes serving as a flow inlet (7) and a flow outlet (8) respectively.

The respective thicknesses of a first (13) and a second (14) silicon membrane, through which the sample emerging orifice (6), the flow inlet (7) and the flow outlet (8) were subsequently etched, were defined by a PN-etch stop process. The depth of the phosphorous doping thus defined the achieved thickness of the first (13) and the second (14) silicon membrane. The sample emerging orifice (6), the flow inlet (7) and the flow outlet (8) were formed by masking the corresponding areas of the first (13) and the second (14) silicon membrane.

Finally the first and second structures (1, 2) were bonded together by silicon direct bonding, whereby the first basin (4) and the second basin (5) together formed a flow channel (3). All angles within the flow channel (3) were made obtuse.

A first silicone tube (11) was glued with silicone rubber gel to the flow inlet (7) and a second silicone tube (12) was glued, also with silicon rubber gel, to the flow outlet (8) in order to provide simple flow connections. A piezo-ceramic disc (9), 8 mm wide and 0.2 mm thick, was glued onto the second silicon membrane (14) between the flow inlet (7) and the flow outlet (8).

The above sampling cell was operated in the following way:

A liquid flow was passed through the sampling cell and as the piezo-ceramic disc (9) was driven by 100 V pulses, 12 µs duration at 1–100 Hz, generated by a pulse generator (10), a continuous drop train emerged from the sample emerging orifice (6). FIGS. 5 and 6 show the drop ejection. The sample emerging orifice (6), having a diameter of 60 µm, yielded a drop diameter of 40 µm, i.e a drop volume of 34 pl. At a pulse frequency of 100 Hz this provided a sample flow of 0.2 µl/min. The size of the drops may be controlled inter alia by the way the pressure pulse is generated.

The operational conditions can be summarized as follows:

The piezo-ceramic disc (9) and the second silicon membrane (14) to which it was glued together formed a bilaminar unit. When a voltage pulse was applied to the disc (9) a bending action was created. Such a bending action is known—see e.g. U.S. Pat. No. 3,747,120 (STEMME). The pressure pulse thereby generated in the flow channel (3) caused a sample drop to be ejected from the sample emerging orifice (6).

Gas bubbles may be encountered in the liquid passing the flow channel (3). This happens e.g. in a liquid arriving from a chromatographic system due to the pressure gradient in the chromatograph column and the decreasing solubility of gas in a liquid with increasing salt concentration. If gas bubbles enter the flow channel (3), the pressure generated by the piezo-ceramic disc (9) may be reduced which in turn may lead to a malfunctioning sampling cell. This phenomena is known from e.g. Ref. 3. To prevent gas bubbles from sticking to the inner walls of the flow channel (3) all angles formed by these inner walls were made to be obtuse. The bubble sticking tendency was further reduced by making the surface of the flow channel (3) non-adherent to gas bubbles through an oxidizing process. The passage of gas bubbles through the flow channel (3) was facilitated by operating the sampling cell in a vertical position with the flow inlet (7) below the flow outlet (8).

It was also important to prevent the outer surface around the sample emerging orifice (6) from being adhered to by the liquid in the flow channel (3), because liquid deposits in the vicinity of the sample emerging orifice (6) may cause drops to be misdirected during ejection. This phenomena is known from i.a. Ref. 2. This problem was solved by operating the sampling cell at a slight negative pressure and/or by making the area surrounding the sample emerging orifice (6) adherent towards the flow channel (3) and non-adherent on the exit side. Capillary forces thereby kept the liquid within the flow cell (3) the liquid meniscus being formed in the sample emerging orifice (6) thereby bending inwards.

EXAMPLE 2

A sampling cell essentially in accordance with Example 1 was used in the following. A glass capillary for capillary electrophoresis was filled with a solution of sodium chloride (NaCl). Through a first end of the capillary was introduced a thin electrically conducting wire for contacting the solution. The second end of the capillary was placed close to the sampling cell, which was filled with ordinary tap water, and subsequently with a sodium chloride solution which did not alter the below described effects. The drop generation was initiated with a drop emerging frequency of around 50 Hz. A high voltage source was connected to the liquid in the sampling cell and to the wire in the first end of the glass capillary. A voltage of about 2500 V was used. When the voltage was applied the emerging drops were attracted by the second end of the glass capillary. The drops did hit the second end surface of the capillary and the outside of the capillary just below this second end surface. By allowing the liquid in the glass capillary to form a small volume extending from the second end of the capillary a more precise hitting of the drops from the sampling cell was achieved. As the electrical force acting on the drops was fairly small it was difficult to influence the direction of the drops when they were close to the sample emerging orifice (6). A larger influence on the drops was achieved when the second end of the glass capillary was moved away some 10 mm from the sample emerging orifice (6) and slightly below this. In this case the velocity of the drops was already reduced and they had started to fall by their own weight.

Further Embodiments

In FIGS. 3, 4 and 6, showing embodiments of the present invention, the flow inlet (7) and the flow inlet (8) are placed on the same surface being opposite the sample emerging orifice (6). It is within the inventive concept to alter the positions of these parts. This means that the flow inlet (7) and the flow outlet (8) may well be placed on opposing surfaces. Likewise may the flow inlet (7) and/or the flow outlet (8) be placed on the same surface as the sample emerging orifice (6).

The actuating means may not be only a piezo-ceramic disc (9), but can also be means making use of e.g. magnetostrictive and/or electromechanical and/or electrostatical forces and/or thermal expansion. The actuating means may consist of one unit, as in Example 1, or a number of units. The actuating means may be placed not only opposite the sample emerging orifice (6), as in Example 1, but also adjacent other parts of the flow channel (3). It is even possible to place the actuating means on the same surface, i.e. corresponding to the first silicon membrane (13) in Example 1, as the sample emerging orifice (6). The flow-through sampling cell can be made entirely of a material which in itself is actuating, such as a piezo-ceramic material with the area around the sample emerging orifice (6) being made of an inert material such as silicon. In such an embodiment there is no need for separate actuating means, such as an piezo-ceramic disc (9) as the cell serves as its own actuator.

By appropriate choice of the geometrical dimensions of the sampling cell mechanical resonance can be reduced or amplified in order to achieve a certain effect on the drop generation. If e.g. the size of the sampling cell is reduced the resonance frequency is increased which leads to increased maximum drop emerging frequency.

If the sampling cell has a fairly thin first silicon membrane (13) the pressure pulses will be dampened due to bending of this membrane (13). Often such dampening is unwanted as the drop generation is thereby disturbed. By making the sampling cell fairly stiff, i.a. by making the first silicon membrane (13) quite thick and thus less bendable, the dampening of the pressure pulse is reduced.

The sample emerging orifice (6) is placed directly in a wall of the flow cell (3), which provides for negligible amounts of liquid remaining in the sample emerging orifice (6) being an advantage e.g. when the sampling cell needs to be cleaned.

The area of adhesion between the liquid in the flow cell (3) during drop ejection and the exit surface of the sample emerging orifice (6) should be as small as possible in order to minimize disturbance on the drop generation. This can be achieved by attaching to the sample emerging orifice (6) a hollow protruding element, such as a short tube or nozzle, extending outwardly from the first silicon membrane (13). The hollow protruding element may also be fabricated directly in the material of the flow-through cell. The free end of such an element should preferably have a very thin or sharp edge, whereby the wetting around this end is minimized and thus also is minimized the disturbance on drop generation. The length of the protruding element should preferably be at least of the same size order as the diameter of the sample emerging orifice (6) in order to achieve a stable direction of the emerging drops. The diameter of the sample emerging orifice (6) can be freely varied up to around 100 $\mu$m. The minimum diameter of the the sample emerging orifice (6) is restricted by the clogging tendency of the fluid which should pass this orifice.

The outside of the sampling cell, especially in the vicinity of the sample emerging orifice (6), can be treated to avoid as much as possible adhesion of the liquid from the flow channel (3), e.g. by coating with an adhesion reducing material. The adhesion can be further reduced if the sample emerging orifice (6), and/or a possible prolonging tube, is provided with small channels or with a porous silicon coating in order to lead away the liquid.

In the above Examples 1 and 2 the sample emerging orifice (6) is placed substantially opposite the piezo-ceramic disc (9) and in the centre of the first basin (4). The sample emerging orifice (6) may very well be placed elsewhere. Further may more than one sample emerging orifice (6) be established in order to achieve multiple trains of emerging drops.

Silicon is a very suitable material for the manufacturing of the present sampling cell. Anyhow other materials such as gallium arsenide, having attractive optical properties, or quartz, being in itself piezo-electrical and allowing UV transmission, may also be used. The known LIGA technique allows for micromaching with totally different materials, such as sintered ceramics, injection moulded polymers or pure metal structures. The LIGA process allows fabrication of microstructures with high aspect ratios and great structural heights by synchrotron radiation litography, galvanoforming and plastic moulding. See Ref. 4. PMMA (polymethyl methacrylate) can be used as phot resist for X-ray exposures. LIGA makes use of PMMA for deep litography. Exposures as deep as several millimeters can be made. LIGA is characterized by extremely high aspect ratios. The developed PMMA exposures may have a thickness of several millimeters with vertical surface roughness in the range of 0.1 $\mu$m. The developed PMMA-exposure can then be submitted to an electroplating procedure, yielding a "negative" metal mould. The metal mould can then be used as a master to fabricate micro-structured devices with extreme aspect ratios in mouldable materials. Very smooth cylindrical holes or tubes can be made to serve as sample emerging orifice (6) in the present flow-through sampling cell.

In the above Examples 1 and 2 the present sampling cell is essentially manufactured from two structures (1, 2). Within the inventive concept it is also possible to manufacture the sampling cell in many other ways, e.g. from three parts—a first thin structure with inlet and outlet, a thick structure with a flow channel and a second thin structure with sample emerging orifice. It is also possible to manufacture the present sampling cell from one piece of material by micro-drilling.

Use of the Invention

The sampling cell according to the present invention may i.e. be used for extracting small, often negligible, samples from a continuous liquid flow;

for extracting a precise sample amount by collecting a defined number of sample drops each having a well-defined volume;

for injecting samples for capillary electrophoresis or electrochromatography. In this case the flow cell is filled with the test liquid and the emerging drops are directed towards the capillary. A suitable number of drops are directed towards the capillary end. The drops may be directed by the application of an electrical field between the flow cell and the capillary opening. The samples can equally well be analyzed through other well known analytical methods, such as slab electrophoresis, mass spectrometry, chemical interaction analysis and liquid chromatography;

for test sampling by splitting of the stream of sampling drops from e.g. liquid chromatography, flow injection analysis, fermentators or reactors to different devices, for e.g. electrophoresis, liquid chromatography, flow injection analysis or chemical interaction analysis;

for very exact drug delivery;

for investigating the reaction velocity between different chemicals entering the flow channel (3) through separate flow inlets (7) and subsequently blending within the flow channel (3);

for simultaneous sampling from different parts of the flow channel (3), e.g. during blending of different chemicals using multiple sample emerging orifices (6);

for evaluating the effects of injecting minute volumes of one liquid into a comparably large volume of another liquid by placing two sampling cells according to the present invention very close to one another the sample emerging orifice (6) of the first cell facing the sample emerging orifice (6) of the second cell. If there is a slight negative pressure in the second cell samples ejected from the first cell are drawn into the liquid in the flow channel (3) of the second cell through its sample emerging orifice (6);

for coating a surface with one or more material(s) in order to achieve a chemically active surface with specific characteristics;

for dispensing different liquids, such as reaction solutions, preferably close to another, by using a multitude of flow-through sampling cells, preferably placed close together. Such dispensing may be simultaneous, consecutive or intermittent;

as a printing device in an ink jet printer, e.g. for printing several colors with just one nozzle by printing the respective colors in series consecutively changing the colored ink in the flow channel.

References

Ref. 1 Nilsson J, Szecsi P. and Schafer-Nielsen C.,
"A flow-through microsampling device applied to an ion exchange chromatography system",
Journal of Biochemical and Biophysical Methods, 27, pp. 181–190, 1993.

Ref. 2 Bentin, H., Doering, M., Radke, W. and Rothgordt, U.,
"Physical properties of micro-planar ink-drop generators",
J. Img. Techn. 12, pp. 152–155, 1986.

Ref. 3 Brock, J. D., Cohen, I. M., Ivanov, I. P., Le, H. P. and Roy, J.,
"Oscillations of an air bubble in an ink jet",
J. Img. Techn. 10, pp. 127–129, 1984.

Ref. 4 E. W. Becker, W. Ehrfeld, P. Hagmann, A. Mauer and D. Münchmeyer
Microelectronic Engineering 4 (1986) 35–36

What is claimed is:

1. A flow-through sampling cell comprising: pressure pulse generating means; and a flow channel with at least one flow inlet, at least one flow outlet and at least one sample emerging orifice, wherein the pressure pulse generating means.

2. The flow-through sampling cell according to claim 1, wherein said sampling cell is made by etching a silicon wafer.

3. The flow-through sampling cell according to claim 1, wherein said sampling cell is made by etching or microstructuring quartz, a piezo-electric material, a piezo-ceramic ceramic or gallium arsenide.

4. The flow-through sampling cell according to claim 1, wherein said sampling cell is made by LIGA technique yielding components comprising of at least one of sintered ceramics, injection molded polymers or metals.

5. The flow-through sampling cell according to claim 1, wherein the flow channel is formed by a first basin in a first structure and a second basin in a second structure.

6. The flow-through sampling cell according to claim 1, wherein said sampling cell reduces the internal sticking of gas bubbles.

7. The flow-through sampling cell according to claim 6, wherein an inside of said flow channel has a form of obtuse angles.

8. The flow-through sampling cell according to claim 6, wherein an inside of said flow channel has a form without angles.

9. The flow-through sampling cell according to claim 1, wherein the pressure pulse generating means comprises at least one selected from the group consisting of a piezo-ceramic element, a device acting by electromechanical force, a device acting by magnetorestrictive force, a device acting by electrostatic forces and a device acting by thermal expansion.

10. The flow-through sampling cell according to claim 1, wherein the flow channel is formed by the pressure pulse generating means.

11. The flow-through sampling cell according to claim 1, wherein the pressure pulse generating means is placed opposite the sample emerging orifice.

12. The flow-through sampling cell according to claim 1, wherein the pressure pulse generating means is placed opposite to the sample emerging orifice, adjacent to the sample emerging orifice, or on the same surface as the sample emerging orifice.

13. The flow-through sampling cell according to claim 1, wherein a hollow protruding element is attached to the sample emerging orifice.

14. The flow-through sampling cell according to claim 13, wherein said hollow protruding element is a short tube or a nozzle.

15. The flow-through sampling cell according to claim 13, wherein said sample emerging orifice is formed as a hollow protruding element.

16. The flow-through sampling cell according to claim 13, wherein a free part of the hollow protruding element ends in a sharp edge.

17. The flow-through sampling cell according to claim 1, wherein at least one of the following treatments is provided:
   (a) an inside of the sampling orifice is treated to increase liquid adhesion; or
   (b) an area surrounding the sampling orifice is treated to decrease liquid adhesion.

18. The flow-through sampling cell according to claim 17, wherein said sampling orifice is treated to decrease liquid adhesion by at least one of the following:
   (a) providing the sampling orifice with a small channel or a porous silicon coating; or
   (b) providing a short tube with a small channel or with a porous silicon coating.

19. The flow-through sampling cell according to claim 1, wherein an outside of the flow-through sampling cell is treated to reduce liquid adhesion.

20. The flow-through sampling cell according to claim 1, wherein the flow-through sampling cell reduces dampening of the generated pressure pulses.

21. The flow-through sampling cell according to claim 20, wherein the dampening of the generated pressure pulses is reduced by making the flow-through sample cell stiff.

22. The flow-through sampling cell according to claim 1, further comprising a controller for controlling the direction of a sample ejected from the sample emerging orifice.

23. The flow-through sampling cell according to claim 22, comprising a device for establishing a difference in electrical potential between a liquid in the flow-through sampling cell and an object to which the sample emerging from the flow-through cell is directed.

24. A method of directing a sample from a flow-through sampling cell according to claim 1, wherein a difference in electrical potential is established between a liquid in the flow-through sampling cell and an object to which the sample emerging from the flow-through cell is directed.

25. A method of coating a surface which comprises:
   providing the flow-through sampling cell according to claim 1; and
   coating the surface, whereby the surface becomes chemically active with specific characteristics.

26. A method of extracting a sample which comprises:
   providing the flow-through sampling cell according to claim 1; and
   extracting the sample from a continuous liquid flow-through the sampling cell.

27. A method of extracting a precise amount of sample which comprises:
   providing the flow-through sampling cell according to claim 1; and
   collecting a defined number of sample drops, wherein each drop has a well-defined volume.

28. A method of injecting a sample into a device for analysis, which comprises:
   providing a device for analysis comprising a flow-through sampling cell according to claim 1; and
   injecting the sample into the device.

29. The method according to claim 28, which further comprises:
   analyzing the sample using a method selected from the group consisting of capillary electrophoresis, slab electrophosesis, electrochromatography, mass spectrometry, chemical interaction analysis and chromatography.

30. A method of dispensing different liquids, which comprises:
   providing a first flow-through sampling cell according to claim 1;
   providing a second flow-through sampling cell according to claim 1; and
   dispensing different liquids from the first flow-through cell and the second flow-through cell, wherein the dispensing may be simultaneous, consecutive or intermittent.

31. A method of injecting a sample into a device for analysis which comprises:
   providing a device for analysis comprising a flow-through sampling device according to claim 1 which comprises a multitude of flow cells; and
   injecting the sample into the device.

32. The method according to claim 31, wherein said multitude of flow-through cells are placed close to one another for injecting different samples.

33. The method according to claim 31, further comprising:
   injecting a plurality of different fluids into a small area.

34. A flow-through sampling cell comprising: pressure pulse generating means; and a flow channel with at least one flow inlet, at least one flow outlet and at least one sample emerging orifice, wherein the pressure pulse generating means generates pressure pulses directly into the flow channel; wherein said flow inlet is below said flow outlet.

35. A flow-through sampling cell comprising:
   pressure pulse generating means; and
   a flow channel with at least one flow inlet, at least one flow outlet and at least one sample emerging orifice, wherein the pulse generating means is placed directly on a surface of the flow channel so that the pressure pulse generating means generates pressure pulses directly into the flow channel.

* * * * *

UNITED STATES PATENT AND TRADEMARK OFFICE
CERTIFICATE OF CORRECTION

PATENT NO.    : 6,192,768 B1
DATED         : February 27, 2001
INVENTOR(S)   : Lars Wallman, Lund, Sweden; Johan Drott, Lund, Sweden; Johan Nilsson, Lund Sweden; Thomas Laurell, Lund, Sweden; and Staffan Nilsson, Lund Sweden.

It is certified that error appears in the above-identified patent and that said Letters Patent is hereby corrected as shown below:

Claim 1,
Should read -- A flow-through sampling cell comprising: pressure pulse generating means; and a flow channel with at least one flow inlet, at least one flow outlet and at least one sample emerging orifice, wherein the pressure pulse generating means generates pulses directly into the flow channel. --

Signed and Sealed this

Fourth Day of December, 2001

*Attest:*

NICHOLAS P. GODICI
*Attesting Officer*      Acting Director of the United States Patent and Trademark Office